United States Patent
Al-Hazmi et al.

(10) Patent No.: US 10,793,502 B2
(45) Date of Patent: Oct. 6, 2020

(54) METHOD OF PURIFYING ACETIC ACID

(71) Applicant: SABIC GLOBAL TECHNOLOGIES B.V., Bergen op Zoom (NL)

(72) Inventors: Mohammed H. Al-Hazmi, Riyadh (SA); Shahid Azam, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/468,516

(22) PCT Filed: Dec. 19, 2017

(86) PCT No.: PCT/IB2017/058094
§ 371 (c)(1),
(2) Date: Jun. 11, 2019

(87) PCT Pub. No.: WO2018/116143
PCT Pub. Date: Jun. 28, 2018

(65) Prior Publication Data
US 2020/0079720 A1    Mar. 12, 2020

Related U.S. Application Data

(60) Provisional application No. 62/436,171, filed on Dec. 19, 2016.

(51) Int. Cl.
*C07C 51/44* (2006.01)
*C07C 51/487* (2006.01)

(52) U.S. Cl.
CPC ............ *C07C 51/44* (2013.01); *C07C 51/487* (2013.01)

(58) Field of Classification Search
CPC .............................. C07C 51/44; C07C 51/487
See application file for complete search history.

(56) References Cited

U.S. PATENT DOCUMENTS 7,208,625 B1 * 4/2007 Wang .................... C07C 51/487
562/608

FOREIGN PATENT DOCUMENTS

| CN | 1562938 A | 1/2005 | |
|---|---|---|---|
| EP | 0294845 A1 | 12/1988 | |
| EP | 0322215 A1 | 6/1989 | |
| EP | 0407091 A1 | 1/1991 | |
| EP | 0480594 A2 | 4/1992 | |
| EP | 0518548 A2 | 12/1992 | |
| EP | 0627401 A1 | 12/1994 | |
| RU | 2440969 C1 | 1/2012 | |
| WO | 9203403 A1 | 3/1992 | |
| WO | WO-9203403 A1 * | 3/1992 | ........... C07C 51/487 |
| WO | 9913980 A1 | 3/1999 | |
| WO | 2016135630 A1 | 9/2016 | |
| WO | WO-2016135630 A1 * | 9/2016 | ........... C07C 51/487 |

OTHER PUBLICATIONS

Acetic Acid, Wikipedia, Acetic Acid, 2020, recovered from internet at https://en.wikipedia.org/wiki/Acetic_acid#Acetaldehyde_oxidation on Mar. 3, 2020, pp. 1-19. (Year: 2020).*
International Search Report issued in Application No. PCT/IB2017/058094, dated Mar. 14, 2018, 5 pages.
Written Opinion issued in Application No. PCT/IB2017/058094, dated Mar. 14, 2018, 6 pages.

* cited by examiner

*Primary Examiner* — Paul A Zucker
(74) *Attorney, Agent, or Firm* — Norton Rose Fulbright US LLP

(57) ABSTRACT

Disclosed herein is a method of purifying acetic acid. The method comprises passing a feed stream comprising acetic acid through a distillation column; contacting the acetic acid with a permanganate oxidizing agent and hydrogen gas within the distillation column; withdrawing an acetic acid product from the distillation column; and withdrawing a gaseous product stream from a top portion of the distillation column, wherein the gaseous product stream comprises ethane, methane, carbon dioxide, oxygen, nitrogen, or a combination comprising at least one of the foregoing.

18 Claims, 1 Drawing Sheet

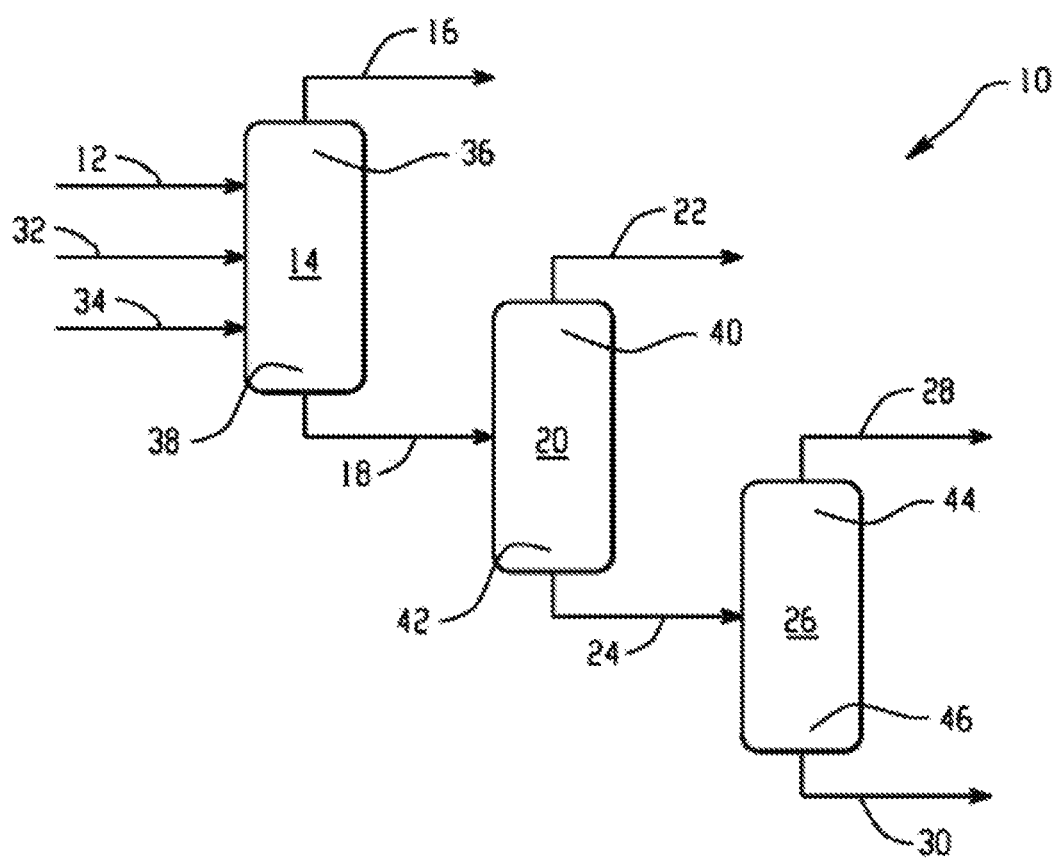

METHOD OF PURIFYING ACETIC ACID

CROSS REFERENCE TO RELATED APPLICATIONS

This application is a National Stage application of PCT/IB2017/058094, filed Dec. 19, 2017, which claims the benefit of U.S. Application No. 62/436,171, filed Dec. 19, 2016, both of which are incorporated by reference in their entirety herein.

BACKGROUND

Ethane, $C_2H_6$, a colorless and odorless hydrocarbon gas at room temperature, is common in nature and can be isolated on an industrial scale during the purification of natural gas or as a byproduct of various petroleum refining processes, such as from catalytic cracking of higher hydrocarbons. The value and/or price of ethane is, however, currently relatively low, either as a fuel, or as a potential feedstock for making other petrochemicals such as ethylene, or acetic acid.

Acetic acid, $CH_3$—$CO_2H$, is a worldwide commodity produced at the level of hundreds of millions of tons per year, as a precursor for vinyl acetate monomer and polymers, and for making various acetate ester solvents and other chemicals. Although many processes for making acetic acid have been developed and commercially employed over the years, acetic acid production by methanol carboxylation is currently dominant in the chemicals industry. In those processes, methane or coal are converted to syngas (mixtures of hydrogen and carbon monoxide), then the syngas is catalytically converted to methanol, which is then reacted with carbon monoxide (separated from syngas) in the presence of rhodium or iridium iodide catalysts, to produce acetic acid. Although modern methanol carboxylation processes are quite efficient, they also require multiple steps and the use of high cost corrosion resistant materials of construction. Therefore, simpler and less capital intensive methods for making acetic acid remain of potential interest to industry, especially since efficient catalysts for hydrogenating acetic acid to make ethanol for use as an automotive fuel component have been discovered recently, so that the continuing expansion of the markets for acetic acid is expected in the long run.

While ethane oxidation processes produce fewer kinds and quantities of impurities heavier than ethanol, ethane oxidation processes also tend to produce relatively high quantities of formic acid, which because of its chemical and physical properties that are similar to acetic acid, is very difficult to separate from acetic acid, particularly to produce very high purity acetic acid containing very low levels of formic acid. Even low levels of formic acid in acetic acid are undesirable because the formic acid promotes corrosion of metal vessels used to make and store acetic acid.

Acetic acid, also known as ethanoic acid, is an organic chemical classified as a simple carboxylic acid. It is an important chemical reagent and industrial chemical useful for the production of various synthetic fibers and other polymeric materials. These polymers include polyethylene terephthalate, used mainly in soft drink bottles; cellulose acetate, used mainly for photographic film; and polyvinyl acetate, for wood glue. In households, diluted acetic acid is often used in descaling agents. The food industry uses it (under the food additive code E260) as an acidity regulator. The global demand for acetic acid has been estimated at around 6.5 million metric tons per year. Of that amount, approximately 1.5 metric tons per year is met by recycling; the remainder is manufactured from petrochemical feedstock or biological sources.

Acetic acid can be produced via a catalytic process, for example, methanol carbonylation. The acetic acid product can often contain undesirable amounts of oxidizable byproducts and impurities. Such contaminated products often fall short of quality testing standards, such as the Permanganate Time Test. Permanganate Time can be used to judge the presence of oxidizable impurities that may be associated with manufacture or contamination during distribution and to assess compliance with a specification. The test involves adding a standard solution of potassium permanganate to the product. Oxidizable impurities discharge the pink permanganate color over a period of time. The standard tests often call for the mixture to be left for periods up to 2 hours before checking the color. If it is still pink, then the sample has passed the test. The presence of such impurities often prevents the acetic acid product from entering into markets with specialized applications and/or restrictions.

Thus, there is a need for an efficient method of purifying acetic acid that can remove oxidizable impurities and produce an acetic acid product that passes the Permanganate Time Test and is therefore appropriate for a wide range of specialized applications.

SUMMARY

Disclosed, in various embodiments, are methods of purifying acetic acid.

A method of purifying acetic acid, comprises: passing a feed stream comprising acetic acid through a distillation column; contacting the acetic acid with an oxidizing agent and hydrogen gas within the distillation column; and withdrawing an acetic acid product from the distillation column.

A method of purifying acetic acid, comprises: passing a feed stream comprising acetic acid through a distillation column; injecting an oxidizing agent and hydrogen gas into a bottom portion of the distillation column, wherein the oxidizing agent is present in a 1 to 50 ratio with the acetic acid and the hydrogen gas is present in a 1 to 50 ratio with the acetic acid; contacting the acetic acid with the oxidizing agent and the hydrogen gas within the distillation column, wherein the oxidizing agent comprises potassium permanganate; withdrawing an acetic acid product from the distillation column, wherein the purity of the acetic acid product is greater than or equal to 98%; passing the acetic acid product through a dehydration column; and passing the acetic acid product through a second distillation column.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

The FIGURE is a schematic diagram representing a reaction scheme in a method for purifying acetic acid.

DETAILED DESCRIPTION

The method disclosed herein can provide an efficient method of purifying acetic acid that can remove oxidizable impurities and produce an acetic acid product that passes the Permanganate Time Test and is appropriate for a wide range of specialized applications. For example, the method can produce an acetic acid product with greater than or equal to 98% purity. The method disclosed herein can also produce an acetic acid product that scores greater than or equal to 2 hours on the Permanganate Time Test. The method can include mixing a strong solid, liquid, or gas oxidant (e.g., potassium permanganate) in a distillation column with a feed stream. Hydrogen gas can be introduced to completely oxidize the impurities. The mixture of water and acetic acid product can then be introduced to a dehydration column where water is boiled off. Acetic acid produced by such a method can have a much higher permanganate time as compared to acetic acid prepared by other methods. Any remaining undesired side products can be removed by polishing the acetic acid in another column.

A method of purifying acetic acid can include passing a feed stream comprising acetic acid through a distillation column. An oxidizing agent and hydrogen gas can be injected into a bottom portion of the distillation column or can be injected into the feed stream together with the feed material. The oxidizing can be present in a 1 to 50 ratio with the acetic acid and the hydrogen gas can be present in a 1 to 50 ratio with the acetic acid. The acetic acid can be contacted with the oxidizing agent and the hydrogen gas within the distillation column. The oxidizing agent can include potassium permanganate. This contact can result in an oxidation reaction, wherein oxidizable impurities present in the feed stream are removed. An acetic acid product can then be withdrawn from the distillation column and further passed through a dehydration column and a second distillation column.

The source of the feed stream can be a catalytic process for producing acetic acid. For example, the source of the feed stream can be a product of a methanol carbonylation process. The source of the feed stream can also be the product of an oxidation process for producing acetic acid. For example, the source of the feed stream can be a product of an acetaldehyde oxidation process and/or an ethane oxidation process.

Ethan oxidation can be carried out in either gas or solution phases, and potentially can employ many potential oxidizing agents for oxidizing ethane such as oxygen gas (which can be alternatively termed diatomic oxygen, or $O_2$), hydrogen peroxide, inorganic peroxides, organic hydroperoxides, or ozone, or mixtures thereof. In another aspect, the oxidation is carried out in the gas phase using oxygen and/or air as an oxidant for ethane, optionally with the addition of one or more additional diluent/carrier gases (water/steam, nitrogen, $CO_2$, methane, and the like).

The feed stream can comprise acetic acid. The feed stream can also comprise by-products and/or impurities. For example, the feed stream can comprise oxidizable impurities, for example, aldehyde impurities and/or carboxylic acid impurities.

The method can include passing the feed stream through a first distillation column. A pressure within the first distillation column can be 0 kiloPascals to 200 kiloPascals, for example 10 kiloPascals to 150 kiloPascals, for example 20 kiloPascals to 100 kiloPascals. A temperature of the first distillation column can be 100° C. to 200° C., for example 110° C. to 175° C., for example 120° C. to 150° C.

An oxidizing agent stream can also be passed through the first distillation column, for example, injected into a bottom portion of the column. For example, the oxidizing agent stream can comprise any desirable oxidizing agent. For example, the oxidizing agent stream can comprise oxygen, air, ozone, fluorine, chlorine, bromine, iodine, hypochlorite, chlorate, nitric acid, chromium trioxide, chromate, dichromate, permanganate, manganite, peroxide, or a combination comprising at least one of the foregoing. For example, the oxidizing agent stream can comprise permanganate, for example, potassium permanganate. The oxidizing agent can be present in a 1:10 to 1:50 ratio with the acetic acid present in the feed stream. For example, the oxidizing agent stream can comprise potassium permanganate in a 1:50 ratio with the acetic acid present in the feed stream.

In one aspect, air is a frequent source for the oxygen gas used to oxidize ethane. In another aspect, air is used as an oxidant, and ethane can be present in an amount of 1% volume (vol) to about 30% vol of ethane, based on the total volume of the crude acetic acid composition, is mixed with air in order to form a feed stream, including exemplary values of 3% vol, 5% vol, 7% vol, 9% vol, 10% vol, 12% vol, 14% vol, 16% vol, 18% vol, 20% vol, 22% vol, 24% vol, 26% vol, and 28% vol. In further aspects, the ethane can be present in an amount of 10% vol to 20% vol based on the total volume of the crude acetic acid composition.

Ethane oxidation can be carried out by combining ethane with oxygen and/or or air in the gas phase, then contacting the resulting ethane/oxygen gas mixture with a solid, liquid, or gaseous catalyst, in a reactor at atmospheric or higher pressures, and at elevated temperatures.

In such ethane oxidation reactions, ethylene ($CH_2$=$CH_2$, sometimes called "ethene") and acetic acid are two major reaction products in the reactions which are believed to occur according to the overall stoichiometry indicated below:

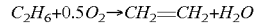

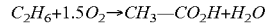

Smaller amounts of other oxygenated organic compounds can also be produced and be present in the reactor product stream vapors, such as carbon monoxide, carbon dioxide, and small amounts of formic acid, acetaldehyde (sometimes called ethanal), ethanol, and some small amounts of higher molecular weight organic oxygenated compounds. If ethane is used as feedstock, higher molecular weight organic oxygenated compounds are typically present at much lower concentrations than if heavier hydrocarbons (such as propane, butanes, pentanes, and hexanes) are used as a feedstock for oxidation.

In one aspect, the ethane oxidation utilizes a catalyst. A variety of catalysts can be employed to improve the rates and selectivity of the ethane oxidation for acetic acid production. A variety of known solid phase catalysts for the gas phase oxidation of ethane to mixtures of acetic acid are known and can be used in the processes described herein. European Patent Publications EP 02 94 845 (catalysts comprising $Mo_xV_yZ_z$ wherein z can be nothing or Nb, Sb, Ta, W etc.), EP 04 80 594 (metal oxide catalysts comprising tungsten, vanadium, rhenium, and an alkali metal), EP 04 07 091 (metal oxide catalysts comprising molybdenum, vanadium, rhenium, and an alkali metal), EP 05 18 548 (catalysts having the empirical formula $VP_aM_bO_x$ where M is one or more of Co, Cu, Re, Nb, W, and others), EP 06 27 401 (catalysts having the formula $V_aTi_bO_x$), and WO 99/13980 (metal oxide catalysts having the formula $Mo_aV_bNb_cX_d$ wherein X is selected from P, B, Hf, Te, and As) describe such catalysts for ethane oxidation, and appropriate combinations of temperature, pressure, mass flow in order to carry out the oxidation of ethane to mixtures of ethylene and acetic acid. Each of the references cited in this paragraph are hereby incorporated by reference for their teachings regarding formulas of the catalyst compositions described therein, their preparations, and conditions for their use in oxidizing ethane. In various aspects of the invention, the catalyst comprises a mixed Mo—V—Nb oxide, and can optionally comprise other metallic components.

A hydrogen stream can further be passed through the first distillation column, for example, injected into a bottom portion of the column. For example, the hydrogen stream can comprise hydrogen gas. For example, the hydrogen gas can be present in a 1:10 to 1:50 ratio with the acetic acid present in the feed stream. For example, the hydrogen gas can be present in a 1:50 ratio with the acetic acid present in the feed stream. The hydrogen stream can aid in oxidation of the feed stream.

The oxidizing agents and/or hydrogen can also be added directly to the feed stream. This can be done as an alternative to the injection of the oxidizing agents and the hydrogen into the first distillation column, or in addition to the injection of these streams into the first distillation column.

The feed stream, oxidizing agent stream, and hydrogen stream can contact each other within the first distillation column. This can result in an oxidation reaction within the first distillation column. For example, an oxidation reaction can occur, wherein oxidizable impurities present within the feed stream are removed.

An acetic acid product stream can then be withdrawn from the first distillation column. For example, the acetic acid product stream can comprise greater than or equal to 95% acetic acid, for example, greater than or equal to 98% acetic acid, along with water and trace impurities. For example, the acetic acid product stream can comprise less than or equal to 0.25 weight % of aldehyde impurities, for example, less than or equal to 0.15 weight %. The acetic acid product stream can also comprise less than or equal to 0.5 weight % heavy carboxylic acid, for example, less than or equal to 0.3 weight %. The acetic acid product can also score greater than or equal to 2 hours on the Permanganate Time Test, thus making it appropriate for a wide range of specialized applications.

A gaseous product stream can also be removed from the first distillation column, for example, from a top portion of the first distillation column. For example, the gaseous product stream can comprise ethane, methane, carbon dioxide, oxygen, nitrogen, or a combination comprising at least one of the foregoing.

The acetic acid product stream can be further passed through a dehydration column. For example, the acetic acid product stream can be dehydrated within the column, wherein the water content of the stream is reduced and the excess water is withdrawn via a water stream. For example, the water stream can be withdrawn from a top portion of the dehydration column. Accordingly, a dehydrated acetic acid product stream can be produced and withdrawn from a bottom portion of the dehydration column.

The dehydrated acetic acid product stream can be further passed through a second distillation column. Any additional trace impurities present in the acetic acid product can be separated within the column and removed via an impurity removal stream from a bottom portion of the column. A final purified acetic acid product stream can then be withdrawn from a top portion of the second distillation column. For example, the final purified product stream can comprise pure acetic acid.

A more complete understanding of the components, processes, and apparatuses disclosed herein can be obtained by reference to the accompanying drawings. These figures (also referred to herein as the "FIGURE" are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Referring now to the FIGURE, this simplified schematic diagram represents a reactor scheme in a method 10 for purifying acetic acid. The reactor scheme 10 can include passing a feed stream 12 through a first distillation column 14. For example, the feed stream 12 can comprise acetic acid and oxidizable impurities. The first distillation column 14 can include a top portion 36 and a bottom portion 38.

An oxidizing agent stream 32 can also be passed through the first distillation column 14. For example, the oxidizing agent stream can comprise potassium permanganate and/or other oxidizing agents as previously described herein. A hydrogen stream 34 can further be passed through the first distillation column 14. For example, the hydrogen stream 34 can comprise hydrogen gas. Oxidizing agents and/or hydrogen can also be added directly to the feed stream 12. This can be done as an alternative to streams 32 and 34, or in addition to streams 32 and 34.

The feed stream 12, oxidizing agent stream 32, and hydrogen stream 34 can contact each other within the first distillation column 14. This can result in an oxidation reaction within the first distillation column 14, wherein oxidizable impurities are removed.

An acetic acid product stream 18 can then be withdrawn from the first distillation column 14. For example, the acetic acid product stream 18 can comprise greater than or equal to 98% acetic acid, along with water and trace impurities. A gaseous product stream 16 can also be removed from the first distillation column 14. For example, the gaseous product stream 16 can comprise ethane, methane, carbon dioxide, oxygen, nitrogen, or a combination comprising at least one of the foregoing.

The acetic acid product stream 18 can be further passed through a dehydration column 20. The dehydration column 20 can include a top portion 40 and a bottom portion 42. For example, the acetic acid product stream 18 can be dehydrated within column 20, wherein water content is reduced and the excess water is withdrawn via water stream 22. Accordingly, a dehydrated acetic acid product stream 24 can be produced and withdrawn from the bottom 42 portion of dehydration column 20.

The dehydrated acetic acid product stream 24 can be further passed through a second distillation column 26. The second distillation column can include a top portion 44 and a bottom portion 46. Any additional trace impurities can be removed from stream 24 via impurity removal stream 30. A final purified acetic acid product stream 28 can then be withdrawn from the top portion 44 of the second distillation column 26.

The methods disclosed herein include(s) at least the following embodiments:

Aspect 1: A method of purifying acetic acid, comprising: passing a feed stream comprising acetic acid through a distillation column; contacting the acetic acid with an oxidizing agent and hydrogen gas within the distillation column; and withdrawing an acetic acid product from the distillation column.

Aspect 2: The method of Aspect 1, wherein a source of the acetic acid is a product of a methanol carbonylation process.

Aspect 3: The method of any of the preceding aspects, wherein a source of the acetic acid is a product of an acetaldehyde oxidation process and/or an ethane oxidation process.

Aspect 4: The method of any of the preceding aspects, wherein the oxidizing agent comprises oxygen, air, ozone, fluorine, chlorine, bromine, iodine, hypochlorite, chlorate, nitric acid, chromium trioxide, chromate, dichromate, permanganate, manganite, peroxide, or a combination comprising at least one of the foregoing.

Aspect 5: The method of Aspect 4, wherein the oxidizing agent comprises permanganate.

Aspect 6: The method of Aspect 5, wherein the oxidizing agent comprises potassium permanganate.

Aspect 7: The method of any of the preceding aspects, wherein the oxidizing agent is present in the feed stream.

Aspect 8: The method of any of the preceding aspects, further comprising injecting the oxidizing agent into a bottom portion of the distillation column.

Aspect 9: The method of any of the preceding aspects, wherein the oxidizing agent is present in a 1 to 10 ratio with the acetic acid.

Aspect 10: The method of any of the preceding aspects, wherein the hydrogen gas is present in a 1 to 50 ratio with the acetic acid.

Aspect 11: The method of Aspect 6, wherein the potassium permanganate is present in a 1 to 50 ratio with the acetic acid.

Aspect 12: The method of any of the preceding aspects, wherein the purity of the acetic acid product is greater than or equal to 98%.

Aspect 13: The method of any of the preceding aspects, wherein the acetic acid product scores greater than or equal to 2 hours on the Permanganate Time Test.

Aspect 14: The method of any of the preceding aspects, wherein a temperature within the distillation column is 120° C. to 150° C.

Aspect 15: The method of any of the preceding aspects, wherein a pressure within the distillation column is 20 kiloPascals to 100 kiloPascals.

Aspect 16: The method of any of the preceding aspects, wherein the acetic acid product contains less than or equal to 0.15 weight % of aldehyde impurities and/or less than or equal to 0.3 weight % heavy carboxylic acid.

Aspect 17: The method of any of the preceding aspects, further comprising passing the acetic acid product through a dehydration column.

Aspect 18: The method of any of the preceding aspects, further comprising passing the acetic acid product through a second distillation column.

Aspect 19: The method of any of the preceding aspects, further comprising withdrawing a gaseous product stream from a top portion of the distillation column, wherein the gaseous product stream comprises ethane, methane, carbon dioxide, oxygen, nitrogen, or a combination comprising at least one of the foregoing.

Aspect 20: A method of purifying acetic acid, comprising: passing a feed stream comprising acetic acid through a distillation column; injecting an oxidizing agent and hydrogen gas into a bottom portion of the distillation column, wherein the oxidizing agent is present in a 1 to 50 ratio with the acetic acid and the hydrogen gas is present in a 1 to 50 ratio with the acetic acid; contacting the acetic acid with the oxidizing agent and the hydrogen gas within the distillation column, wherein the oxidizing agent comprises potassium permanganate; withdrawing an acetic acid product from the distillation column, wherein the purity of the acetic acid product is greater than or equal to 98%; passing the acetic acid product through a dehydration column; and passing the acetic acid product through a second distillation column.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of purifying acetic acid, comprising:
   passing a feed stream comprising acetic acid through a distillation column;
   contacting the acetic acid with a permanganate oxidizing agent and hydrogen gas within the distillation column;
   withdrawing an acetic acid product from the distillation column; and
   withdrawing a gaseous product stream from a top portion of the distillation column, wherein the gaseous product stream comprises ethane, methane, carbon dioxide, oxygen, nitrogen, or a combination comprising at least one of the foregoing.

2. The method of claim 1, wherein the source of the acetic acid is a product of a methanol carbonylation process.

3. The method of claim 1, wherein the source of the acetic acid is a product of an acetaldehyde oxidation process and/or an ethane oxidation process.

4. The method of claim 1, wherein the oxidizing agent comprises oxygen, air, ozone, chlorine, bromine, iodine, hypochlorite, chlorate, nitric acid, chromium trioxide, chromate, dichromate, manganite, peroxide, or a combination comprising at least one of the foregoing.

5. The method of claim 1, wherein the oxidizing agent comprises potassium permanganate.

6. The method of claim 1, wherein the oxidizing agent is present in the feed stream.

7. The method of claim 1, further comprising injecting the oxidizing agent into a bottom portion of the distillation column.

8. The method of claim 1, wherein the oxidizing agent is present in a 1 to 10 molar ratio with the acetic acid.

9. The method of claim 1, wherein the hydrogen gas is present in a 1 to 50 molar ratio with the acetic acid.

10. The method of claim 5, wherein the potassium permanganate is present in a 1 to 50 molar ratio with the acetic acid.

11. The method of claim 1, wherein the purity of the acetic acid product is greater than or equal to 98%.

12. The method of claim 1, wherein the acetic acid product scores greater than or equal to 2 hours on the Permanganate Time Test.

13. The method of claim 1, wherein the temperature within the distillation column is 120° C. to 150° C.

14. The method of claim 1, wherein the pressure within the distillation column is 20 kiloPascals to 100 kiloPascals.

15. The method of claim 1, wherein the acetic acid product contains less than or equal to 0.15 weight % of aldehyde impurities and/or less than or equal to 0.3 weight % carboxylic acid impurities.

16. The method of claim 1, further comprising passing the acetic acid product through a dehydration column.

17. The method of claim 1, further comprising passing the acetic acid product through a second distillation column.

18. A method of purifying acetic acid, comprising:
   passing a feed stream comprising acetic acid through a distillation column;
   injecting an oxidizing agent and hydrogen gas into a bottom portion of the distillation column, wherein the oxidizing agent is present in a 1 to 50 molar ratio with the acetic acid and the hydrogen gas is present in a 1 to 50 molar ratio with the acetic acid;
   contacting the acetic acid with the oxidizing agent and the hydrogen gas within the distillation column, wherein the oxidizing agent comprises potassium permanganate;
   withdrawing an acetic acid product from the distillation column, wherein the purity of the acetic acid product is greater than or equal to 98%;
   withdrawing a gaseous product stream from a top portion of the distillation column, wherein the gaseous product stream comprises ethane, methane, carbon dioxide, oxygen, nitrogen, or a combination comprising, at least one of the foregoing:
   passing the acetic acid product through a dehydration column; and
   passing the acetic acid product through a second distillation column.

* * * * *